United States Patent [19]
Takahashi

[11] Patent Number: 5,557,454
[45] Date of Patent: Sep. 17, 1996

[54] STEREOSCOPIC ENDOSCOPE

[75] Inventor: Susumu Takahashi, Iruma, Japan

[73] Assignee: Olympus Optical Co., Ltd., Tokyo, Japan

[21] Appl. No.: 139,804

[22] Filed: Oct. 22, 1993

[30] Foreign Application Priority Data

Dec. 25, 1992 [JP] Japan ................... 4-347023
Dec. 28, 1992 [JP] Japan ................... 4-348065

[51] Int. Cl.⁶ .................. G02B 21/22; G02B 27/22; A61B 1/04
[52] U.S. Cl. .................. 359/378; 359/377; 359/376; 359/464; 348/45
[58] Field of Search ................... 348/45, 65; 359/468, 359/473, 464, 377, 376, 378, 379, 385, 462

[56] References Cited

U.S. PATENT DOCUMENTS

| | | | |
|---|---|---|---|
| 4,364,629 | 12/1982 | Lang et al. ........................ | 359/377 |
| 4,862,873 | 9/1989 | Yajima et al. ..................... | 128/6 |
| 5,295,477 | 3/1994 | Janfaza ........................... | 359/385 |

FOREIGN PATENT DOCUMENTS 2919678  11/1980  Germany .
57-69839  4/1982  Japan .

*Primary Examiner*—Paul M. Dzierzynski
*Assistant Examiner*—Audrey Chang
*Attorney, Agent, or Firm*—Armstrong, Westerman, Hattori, McLeland & Naughton

[57] ABSTRACT

A stereoscopic endoscope comprises an objective lens array having one optical axis, a relay lens array for transmitting an object image produced by the objective lens array, a pupil split element that is located at an entrance pupil position of the relay lens array; that is, a position at which the relay lens array forms an entrance pupil, a position near the entrance pupil position, or a position conjugate with those positions, and that splits an entrance pupil formed by the relay lens array into a plurality of portions, an image formation optical system that receives a beam emanating from the relay lens array and forms a plurality of object images in cooperation with the pupil split element, and imaging devices for receiving the object images.

18 Claims, 10 Drawing Sheets

STEREOSCOPIC ENDOSCOPE

BACKGROUND OF THE INVENTION

1. Field of the Invention

The present invention relates to a stereoscopic endoscope enabling three-dimensional observation of a region to be observed.

2. Description of the Related Art

An endoscope system, of which an elongated insertional part can be inserted into a body cavity to observe a region to be examined that cannot be viewed directly, has been widely adopted. A standard endoscope system can merely visualize a region to be examined as a planar image providing no depth perception. It is therefore hard to observe fine irregularities on the surface of the wall of a body cavity, which makes it difficult to make diagnosis or give various kinds of treatment during observation under endoscopic guidance.

To overcome the foregoing drawback, a plurality of observation optical systems may be set in array. These observation optical systems are arranged so that the optical axes thereof will create an angle of convergence and thus have a parallax between them, thus permitting three-dimensional visualization of a region to be observed.

In this type of stereoscopic endoscope system disclosed in, for example, Japanese Patent Laid-Open No. 57-69839, a pair of image transmission optical systems are installed in an insertional part of an endoscope, a pair of objective optical systems are installed in distal parts of the image transmission optical systems, and a pair of eyepiece optical systems are installed in a proximal operational part of the endoscope. An angle of convergence created by the pair of objective optical systems is adjusted so that a region to be observed can be seen three-dimensionally.

FIG. 1 shows a schematic configuration of a conventional stereoscopic endoscope. A stereoscopic endoscope 51 has two objective lens arrays 52a and 52b, and two relay lens arrays 53a and 53b for transmitting images formed by the objective lens arrays 52a and 52b in the distal part of an elongated insertional part thereof. The respective images are picked up by solid-state imaging devices 54a and 54b that may be CCDs.

In a stereoscopic endoscope, if the right and left images formed by two optical systems are distorted even slightly, a plane region is seen waxing or waning. The visualized image can therefore not be said to have true three-dimensionality. For normal three-dimensional visualization, it is a must to prevent an optical system from distorting an image.

A rather wide-angle optical system is needed to recognize the location of a observed region in the whole of a subject. The wide-angle optical system cannot help causing distortion in the perimeter of an image from the designing and manufacturing viewpoints.

For normal three-dimensional visualization, it is required to prevent right and left optical systems from distorting images. In a stereoscopic endoscope having wide-angle optical systems, distortion occurs in the perimeters of images from the designing and manufacturing viewpoints. Thus, normal three-dimensional visualization has not yet been realized.

When an attempt is made to realize normal three-dimensional visualization, a wide-angle optical system cannot be employed. All observation images have therefore come to show narrow fields of view. When a wide-angle optical system is used to exhibit a wide field of view, normal three-dimensionality is unavailable because of distortion in the perimeters of observation images. This necessitates the use of a stereoscopic endoscope that can provide a rather wide-angle field of view which aids in recognition of the location of a region to be observed in the whole of a subject and permits normal three-dimensional visualization of an object region to be observed.

In the conventional stereoscopic endoscope shown in FIG. 1, when the distance to a subject changes, the angle of convergence varies. When a subject approaches, the angle of convergence becomes larger as indicated with a dashed line in FIG. 1 and the three-dimensionality improves. When the subject goes away, the three-dimensionality deteriorates. That is to say, three-dimensionality varies depending on the distance to a subject.

For example, when a stereoscopic endoscope is employed for a surgical procedure, a surgeon wants to proceed with the procedure while having the same sense of three-dimensionality irrelevant of whether he/she observes a region to be examined at a near point or a far point. The aforesaid stereoscopic endoscope, in which three-dimensionality improves at a near point but deteriorates at a far point, cannot satisfy the foregoing demand from surgeons.

As mentioned above, in the conventional stereoscopic endoscope, the angle of convergence varies depending on the distance to a subject and the three-dimensionality of a produced image changes. Observation cannot therefore be carried on with the same sense of three-dimensionality.

In contrast, it is also demanded to observe a subject with a sense of three-dimensionality that ensures comfortable seeing and differs between a near point and a far point. In the past, it has also been difficult to control three-dimensionality and thus provide a desired sense of three-dimensionality for a certain distance to an object.

As described above, a stereoscopic endoscope should be able to control three-dimensionality optimally according to a distance to a subject and a position in a field of view, and visualize an intended region to be observed normally and three-dimensionally while exerting the desired three-dimensionality. The conventional configuration can hardly realize such a stereoscopic endoscope.

SUMMARY OF THE INVENTION

An object of the present invention is to provide a stereoscopic endoscope capable of providing an optimal sense of three-dimensionality according to a distance to a subject and a position in a field of view.

Another object of the present invention is to provide a stereoscopic endoscope capable of offering a rather wide-angle field of view to enable recognition of the whole of a subject and visualizing an intended region to be observed normally and three-dimensionally.

Yet another object of the present invention Is to provide a stereoscopic endoscope that can control three-dimensionality of a produced image if necessary and that can perform three-dimensional visualization with desired three-dimensionality irrelevant of a distance to a subject.

The present invention comprises an objective lens array having a single optical axis, a relay lens array for transmitting an object image formed by the objective lens array, a pupil split means that is located at an entrance pupil position of the relay lens array that is a position at which the relay lens array forms an entrance pupil, a position near the entrance pupil position, or a position conjugate with these positions, and that splits the entrance pupil into a plurality of portions, an image formation optical system that receives a beam emanating from the relay lens array and forms a plurality of object images in cooperation with the pupil split means, and imaging means for receiving the object images.

Other features and advantages of the present invention will be fully apparent from the description below.

BRIEF DESCRIPTION OF THE DRAWINGS

FIG. 2 is an explanatory diagram showing the appearance of a stereoscopic endoscope;

FIG. 3 is an explanatory diagram showing a configuration of a major portion of the stereoscopic endoscope;

FIG. 4 is an explanatory diagram showing the state of an entrance pupil that varies depending on the position in a field of view and thus explaining the operation of the stereoscopic endoscope;

FIGS. 5 and 6 relate to the second embodiment of the present invention;

FIG. 5 is an explanatory diagram showing a configuration of a major portion of a stereoscopic endoscope;

FIGS. 7 to 9 relate to the third embodiment of the present invention;

FIG. 7 is an explanatory diagram showing a configuration of a major portion of a stereoscopic endoscope;

FIG. 11 is an explanatory diagram showing a configuration of a major portion of a stereoscopic endoscope;

FIG. 12 is an explanatory diagram showing the light passing through variable diaphragms via a pupil split prism;

FIG. 13 is an oblique view schematically showing a configuration of variable diaphragms.

DETAILED DESCRIPTION OF THE PREFERRED EMBODIMENTS

Figure 1:
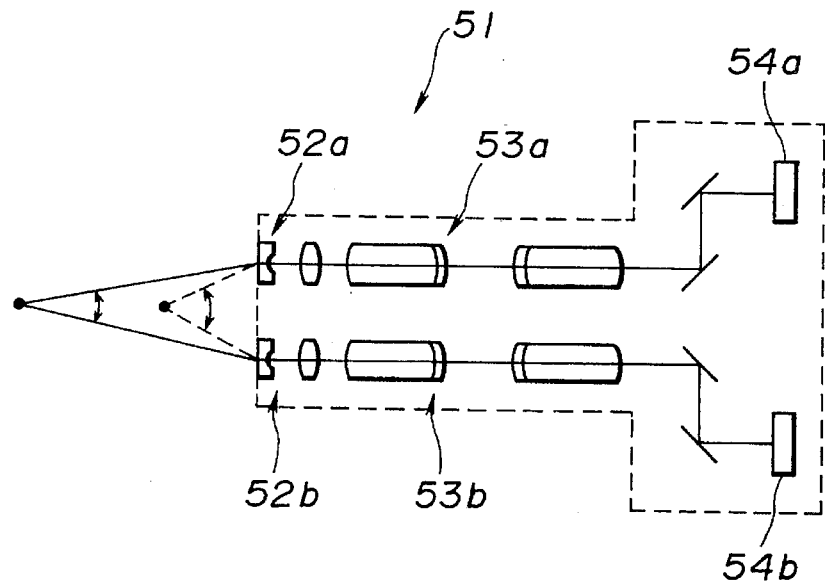
FIG. 1 is an explanatory diagram showing an example of a configuration of a conventional stereoscopic endoscope.
Figure 2:
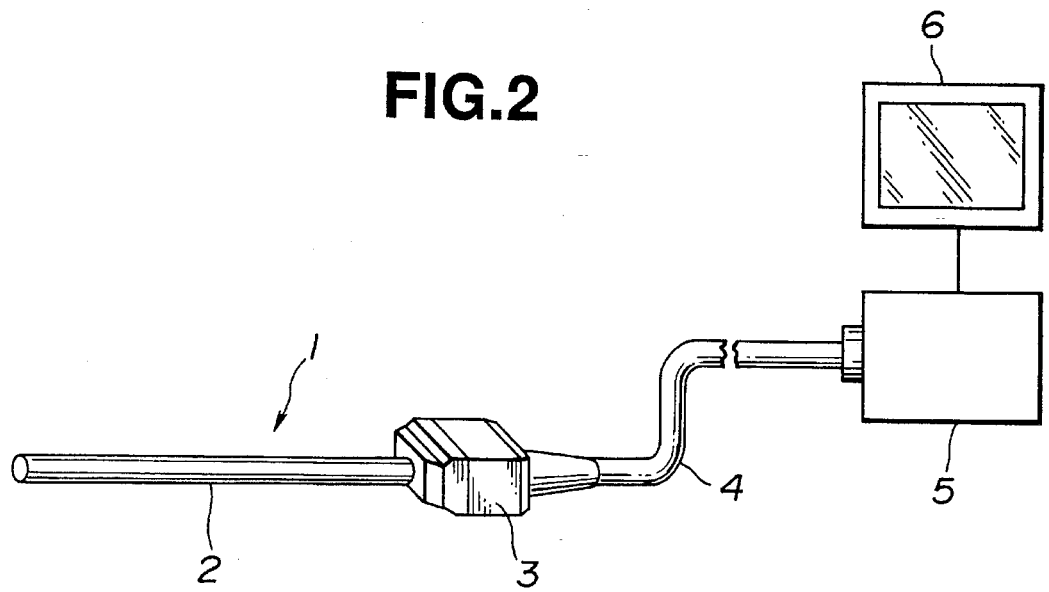
FIGS. 2 to 4 relate to the first embodiment of the present invention.
Figure 3:
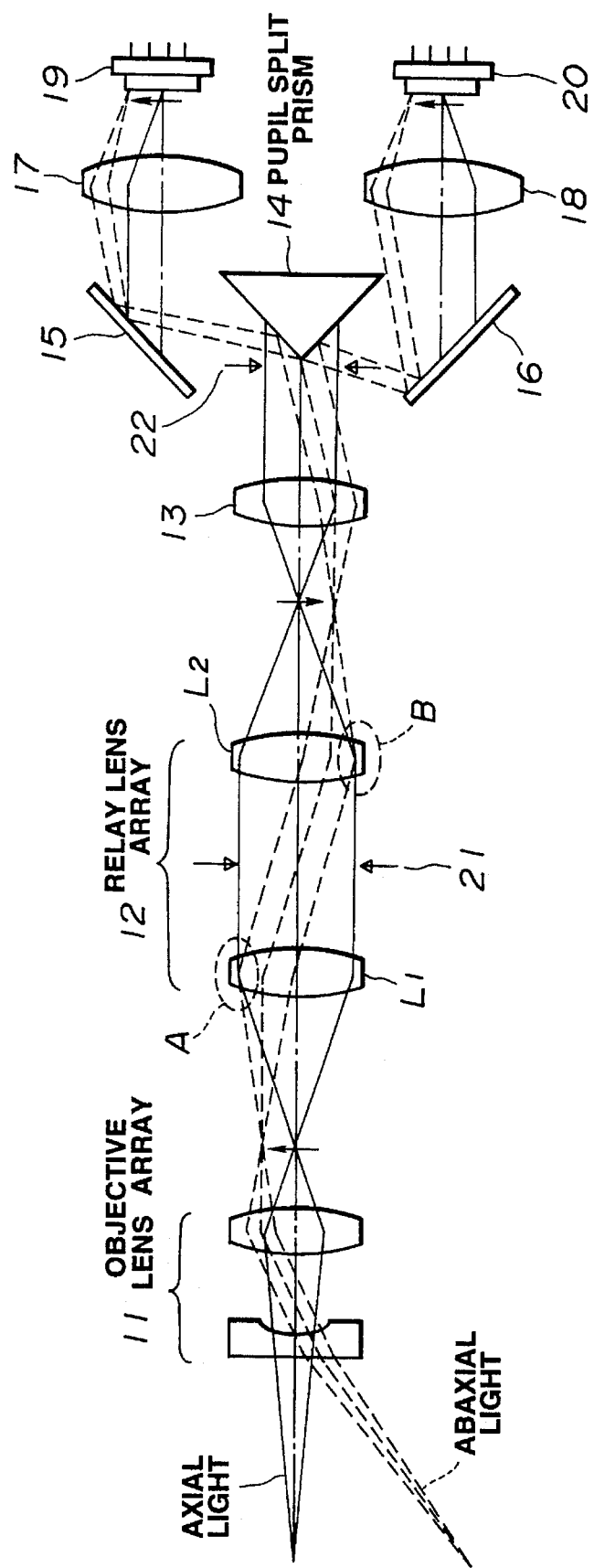
Figure 4:
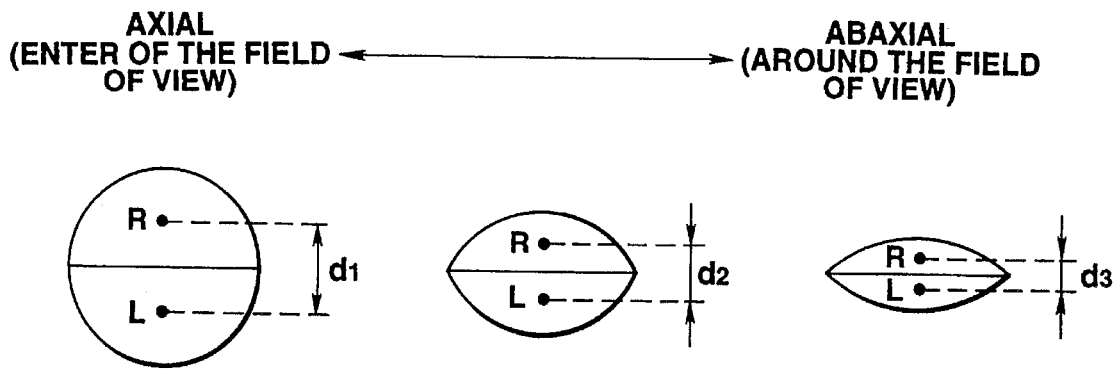

FIGS. 2 to 4 show the first embodiment of the present invention.

As shown in FIG. 2, a stereoscopic endoscope 1 (which may hereafter be referred to as an endoscope) has an elongated insertional part 2. A grip 3 is attached to the proximal end of the insertional part 2. A cable 4 extends from the grip 3. The stereoscopic endoscope 1 is connected to a signal processing unit 5 over the cable 4. A display unit 6 such as a CRT monitor is connected to the signal processing unit 5. Right and left observation images produced by the endoscope 1 are processed by the signal processing unit 5 and displayed as a three-dimensional endoscopic image on the display unit 6. For example, two images of right and left images are displayed alternately on the display unit 6. When viewing the two images with polarizing glasses, a three-dimensional image of a subject can be observed.

The major portion of the stereoscopic endoscope 1 including an optical system is configured as shown in FIG. 3. One objective lens array 11 is installed in the distal part of the endoscope 1. A relay lens array 12 for transmitting a subject image formed by the objective lens array 11 is located behind the objective lens array 11 coaxially with the objective lens array 11. A first image formation lens 13 and a pupil split prism 14 serving as a pupil split means are arranged behind the relay lens array 12, whereby the image transmitted by the relay lens array 12 is halved right and left. Specifically, an image produced by the objective lens array 11 having one optical axis is transmitted by the relay lens array 12 and halved into right and left images by the pupil split prism 14. Thus, an entrance pupil formed in the optical system is split.

Mirrors 15 and 16 and second image formation lenses 17 and 18 are included. The light split by the pupil split prism 14 is reflected by the mirrors 15 and 16, and converged on the second image formation lenses 17 and 18 so as to form images. That is to say, the first image formation lens 13, and the second image formation lenses 17 and 18 constitute an image formation optical system.

Solid-state imaging devices 19 and 20 serving as imaging means, such as CCDs, are located at the image formation positions of the second image formation lenses 17 and 18, that is, the positions at which the second image formation lenses 17 and 18 form images. The subject images formed on the imaging surfaces of the solid-state imaging devices 19 and 20 are subjected to photoelectric transfer. Resultant electric signals are output as pickup signals. The output signals of pickup signals are sent to the signal processing unit 5 and subjected to various kinds of image signal processing so as to be displayed on the display unit 6. Consequently, endoscopic images of a subject are displayed on the display unit 6.

In the optical system of the stereoscopic endoscope 1, the relay lens array 12 is composed of afocal relay lenses each projecting an output image with the magnification unchanged. FIG. 3 shows two lenses for simplification. Assuming that a leading lens in the relay lens array 12 is $L_1$ and a trailing lens is $L_2$, the relay lens array 12 is arranged so that the back focus of the lens $L_1$ will align with the front focus of the lens $L_2$. The relay lens array 12 is located back and forth an entrance pupil 21 and arranged optically symmetrically with respect to the entrance pupil 21. Moreover, a portion A exerting the vignetting effect by removing the upper part of abaxial light and a portion B exerting the vignetting effect by removing the lower part of abaxial light, which serve as beam restricting means, are located symmetrically with respect to the entrance pupil 21. In other words, the relay lens array 12 exerts the effects that the entrance pupil formed with the axial light indicated with solid lines in FIG. 3 will differ in size from that formed with the abaxial light indicated with dashed lines, and that the entrance pupil will remain symmetric up and down in FIG. 3 (corresponding to the right and left images deriving from the split entrance pupil).

The pupil split prism 14 is arranged so that the apex of the prism, at which an image is split, will come at a position 22 conjugate with an entrance pupil formed by the objective lens array 11 and relay lens array 12; that is, at a position at which an aperture stop Is installed.

The location of the pupil split prism 14 is not limited to the position conjugate with an entrance pupil formed by the objective lens array 11 and relay lens array 12, but may be an entrance pupil position; that is, a position at which an entrance pupil is formed, or a position near the entrance pupil position.

Next, the operation of the present embodiment will be described.

For normal three-dimensional visualization, an optical system must be designed not to distort right and left images. When a wide-angle optical system is employed so as to enable recognition of the location of an observed region in the whole of a subject, distortion occurs in the perimeters of images. This prevents true three-dimensional visualization.

It is, however, only a limited range around the center of a field of view that must be visualized three-dimensionally, and the perimeter of the field of view should not necessarily be seen three-dimensionally. This embodiment is designed to deteriorate three-dimensionality in visualizing the perimeter of a field of view whose image is too distorted to be seen three-dimensionally. Thus, the distortion in the images showing the perimeter of a field of view will not affect observation images very much. A wide-angle optical system can therefore be employed to provide a wide field of view, and normal three-dimensional visualization can be done with the images showing the center of the field of view.

The pupil split prism 14 halves an entrance pupil to provide right and left images having a parallax between them. In this case, as long as a split entrance pupil provides the same diameter and same split ratio irrelevant of whether light originates from the center or perimeter of a field of view, an interval between the centers of gravity in the right and left images deriving from the split entrance pupil will remain constant irrelevant of the position in a field of view from which light originates, and three-dimensionality will not vary depending on whether light originates from the center or perimeter of a field of view.

When the entrance pupil is shaped like a circle as shown in the left of FIG. 4, the foregoing interval between the centers of gravity is defined as an interval between the center of gravity in one of semicircular halves of the split circular entrance pupil and that of the other semicircle. Three-dimensionality varies depending on the interval between centers of gravity. As the interval between centers of gravity becomes smaller, a parallax decreases to deteriorate three-dimensionality. When the interval between centers of gravity is zero, that is, the centers of gravity of two images align with each other, a monophonic image ensues.

In this embodiment, the interval between centers of gravity shall vary depending on whether light originates from the center or perimeter of a field of view: when light originates from the center of a field of view, the interval between centers of gravity shall be large, while when light originates from the perimeter of a field of view, the interval between centers of gravity shall be small. This is intended to preserve three-dimensionality for light originating from the center of a field of view but deteriorate three-dimensionality for light originating from the perimeter thereof.

To materialize the foregoing principle, in this embodiment, the relay lens array 12 forms a smaller entrance pupil with light originating from the perimeter of a field of view. Thus, the interval between centers of gravity in right and left images deriving from the split entrance pupil varies. More particularly, the portion A of the leading lens $L_1$ in the relay lens array 12 removes the upper part of abaxial light, and the portion B of the trailing lens $L_2$ removes the lower part of the abaxial light. Thus, the diameter of the entrance pupil in a direction perpendicular to the split line of the entrance pupil is shrunken as shown in the right of FIG. 4.

The leading lens $L_1$ and trailing lens $L_2$ in the relay lens array 12 are arranged mutually symmetrically with respect to the entrance pupil position, whereby the upper and lower parts of abaxial light are removed symmetrically. The pupil split prism 14 should therefore be located at a position conjugate with an entrance pupil formed by the objective lens array 11 and relay lens array 12. Since the symmetry of the entrance pupil is preserved, when the entrance pupil is split in the center thereof by the pupil split prism 14, the entrance pupil is split laterally symmetrically all the time. The entrance pupil formed by the relay lens array 12 therefore varies in size, as shown in FIG. 4, depending on whether it derives from axial or abaxial light, or intermediate light that comes from an intermediate position between the positions from which the axial and abaxial light originate. The diameter of the entrance pupil in a direction perpendicular to the split line thereof decreases in the order of axial, intermediate, and abaxial light. Accordingly, the interval between centers of gravity in right and left images deriving from a split entrance pupil decreases from $d_1$ through $d_2$ to $d_3$. Thus, the interval between centers of gravity becomes the smallest with light originating from the perimeter of a field of view.

As mentioned above, since the interval of centers of gravity in right and left images deriving from a split entrance pupil is varied, when light originates from the perimeter of a field of view, the parallax between the right and left images decreases. Three-dimensionality deteriorates accordingly, whereby an image formed with the light originating from the perimeter of a field of view becomes almost like a monophonic image.

According to this embodiment, the interval between centers of gravity in right and left images deriving from an entrance pupil is varied depending on the position in a field of view from which light originates, whereby three-dimensionality is deteriorated in an image of the perimeter of a field of view. This helps minimize the influence of distortion that is likely to occur in an image of the perimeter of a field of view. Thus, this embodiment provides a stereoscopic endoscope capable of providing normal three-dimensionality for an image of the center of a field of view and offering a wide field of view that is wide enough to grasp entire object.

In other words, this embodiment exerts the effect of providing a moderately wide field of view that is wide enough to recognize the whole of an object and enabling normal three-dimensional visualization of an intended region to be observed.

Figure 6A:
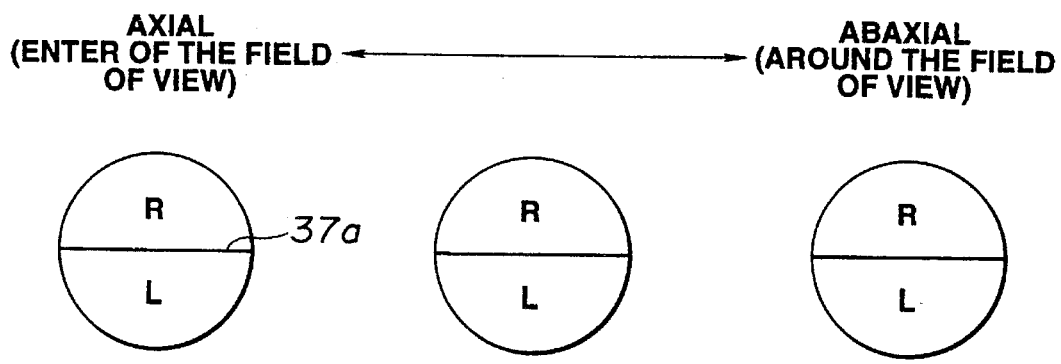
FIGS. 6(a) and 6(b) are an explanatory diagrams showing the state of an entrance pupil that varies depending on the position in a field of view and thus explaining the operation of the stereoscopic endoscope.
Figure 6B:
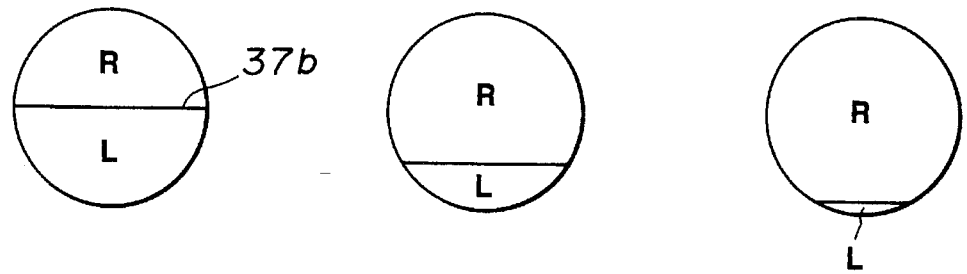
Figure 5:
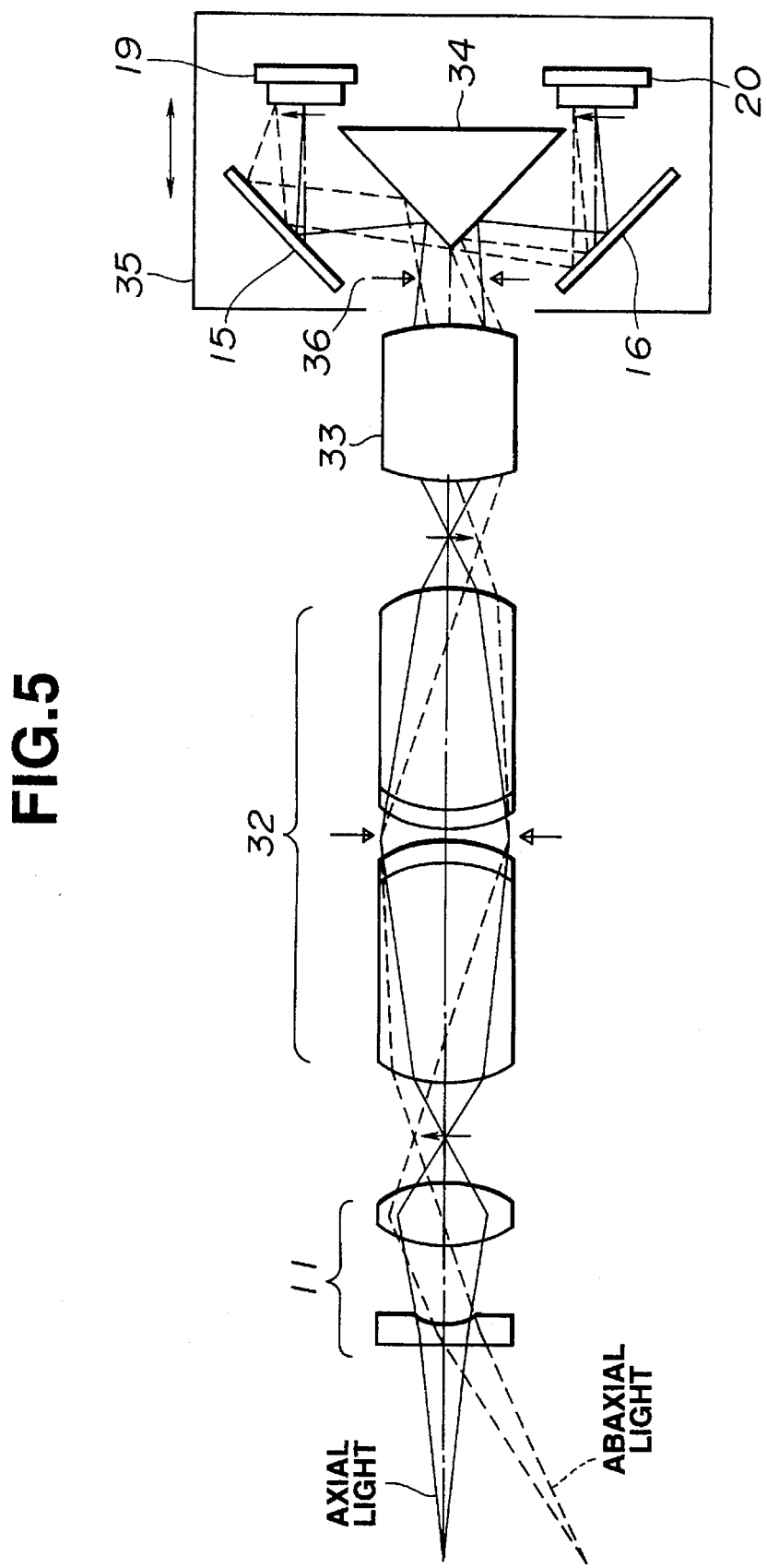

FIGS. 5 and 6(a), 6(b) show the second embodiment of the present invention.

In the second embodiment, the split ratio of a left image to a right image of an entrance pupil formed in an optical system is varied.

A major portion including an optical system of a stereoscopic endoscope of this embodiment has a configuration shown in FIG. 5. A relay lens array 32 that, unlike the one in the first embodiment, will not change the diameter of an entrance pupil according to the position in a field of view from which light originates is installed behind an objective lens array 11. An image formation lens 33 is located behind the relay lens array 32. A pupil split prism 34, which halves an image transmitted by the relay lens array 32 and formed by the image formation lens 33 into right and left images, is installed behind the image formation lens 33. The image formation lens 33 includes a zoom lens array made up of, for example, a compensator, a variation lens, and a relay lens. In FIG. 5, only one lens is shown as the image formation lens 33 for simplification.

In addition, mirrors 15 and 16 are included to reflect beams deriving from the light split by the pupil split prism 34. Solid-state imaging devices 19 and 20 are also installed to receive the beams reflected by the mirrors 15 and 16 and pick up electric signals therefrom.

The pupil split prism 34, mirrors 15 and 16, and solid-state imaging devices 19 and 20 constitute a mobile unit 35 that is movable in a united body. The mobile unit 35 is movable back and forth on the optical axis relative to a position 36 conjugate with an entrance pupil formed in the optical system (or entrance pupil position that is a position at which an entrance pupil is formed). Normally, as shown in FIG. 5, the apex of the pupil split prism 34 is located slightly behind the entrance pupil position 36. The pupil split prism 34 is located slightly away from the entrance pupil position 36 along the optical axis, so that the split position at which an entrance pupil is split can be varied between axial light indicated with solid lines in FIG. 5 and abaxial light indicated with dashed lines.

The pupil split prism 34 may be located not only at a position conjugate with an entrance pupil formed in an optical system but also at a position near the entrance pupil position.

When the pupil split prism 34 is used to halve an entrance pupil and produce right and left images having a parallax between them, if the pupil split prism 34 is located at the position conjugate with the entrance pupil formed by the objective lens array 11 and relay lens array 32, a boundary 37a between the right and left images, as shown in FIG. 6a, aligns with the center line of the split entrance pupil irrelevant of the position in a field of view from which light originates. The entrance pupil is therefore split laterally symmetrically all the time.

When the pupil split prism 34 is located slightly away from the entrance pupil position or the position conjugate with an entrance pupil, as shown in FIG. 5, abaxial light enters askew the pupil split prism 34. An entrance pupil is therefore not split in the center thereof. As shown in FIG. 6b, when light originates from the center of a field of view, a boundary between right and left images deriving from a split entrance pupil lies in the center of the entrance pupil. When light originates from the perimeter of a field of view, the boundary 37b moves toward left or right (toward the left in FIG. 6b).

When the split position of an entrance pupil is varied depending on the position in a field of view, if light originates from the perimeter of a field of view, the quantities of light in right and left images deriving from an entrance pupil become markedly unbalanced. Three-dimensionality thus deteriorates and an almost monophonic image ensues. That is to say, the image looks substantially like the one viewed with one eye.

The ratio of the quantity of light in a right image to that in a left image of a split image is set to 1 to 1 for light originating from the center of a field of view, and 1 to 0 for light originating from the perimeter of a field of view. That is to say, when light is abaxial light, the beam is concentrated on either right or left images. Thus, three-dimensionality is deteriorated in an image of the perimeter of a field of view. When the split ratio of quantities of light exceeds 1 to 0.3; that is, when the quantities of light in right and left images are markedly unbalanced, substantially monophonic seeing ensues. In an optical system that despite light originating from the center or perimeter of a field of view, produces an entrance pupil having the same diameter, the split ratio of quantities of light in an entrance pupil is 1 to 1 for light originating from the center of a field of view. The split ratio becomes larger than 1 to 0.3 (for example, 1 to 0.2) for light originating from the perimeter of a field of view (the difference in quantity of light between two images deriving from a split entrance pupil becomes larger). When the pupil split prism 34 is located slightly away from the entrance pupil position, as mentioned above, if light originates from the perimeter of a field of view, three-dimensionality deteriorates.

As described above, in this embodiment, the split ratio of a quantity of light; that is, a ratio of the quantity of light in a right image to that in a left image is varied depending on the position in a field of light from which light originates. In this embodiment, similarly to the first embodiment, when light originates from the perimeter of a field of view, three-dimensionality deteriorates. Thus, the influence of distortion in an image, which usually attributes to light originating from the perimeter of a field of view, can be minimized. Thus, this embodiment materializes a stereoscopic endoscope that provides normal three-dimensionality for light originating from the perimeter of a field of view and offers a wide field of view which is wide enough to grasp the whole of an object.

The optical system in the first or second embodiment may further include an image formation lens, a focusing lens, a zoom lens, or the like.

FIGS. 7 to 9(a), 9(b) show the third embodiment of the present invention.

Figure 7:
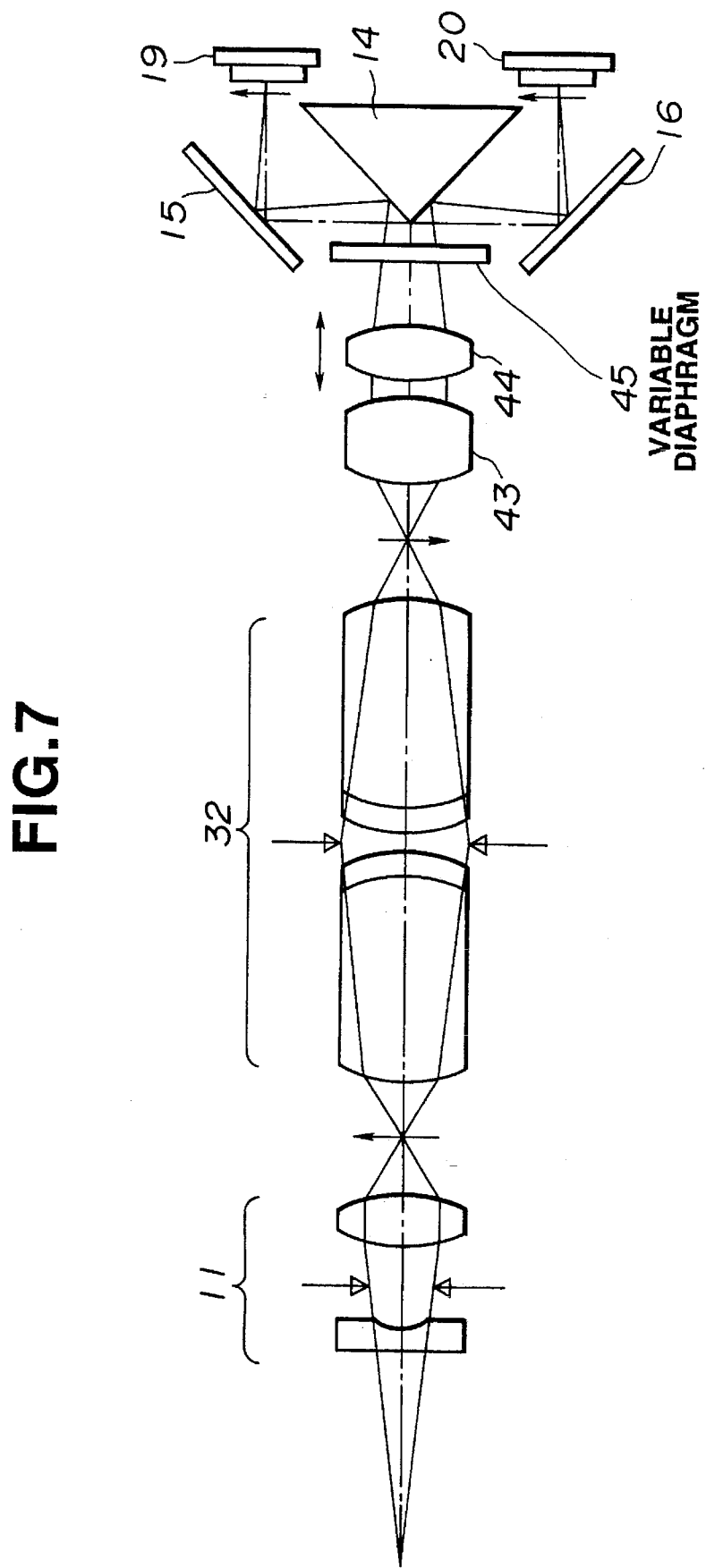

A major portion including an optical system of a stereoscopic endoscope of this embodiment has a configuration shown in FIG. 7.

One object lens array 11 is installed in the distal part of an endoscope 1. A relay lens array 32, which is similar to the one in the second embodiment, for transmitting a subject image formed by the objective lens array 11 is installed coaxially with the objective lens array 11 behind the objective lens array 11. An image formation lens 43 and a focusing lens 44 are arranged behind the relay lens array 32. A pupil split prism 14 for halving a transmitted and formed image into right and left images is located at a position which is conjugate with the entrance pupil formed by the objective lens array 11 and relay lens array 32, behind the focusing lens 44.

A variable diaphragm 45 for varying the interval between centers of gravity in images deriving from a split entrance pupil is installed in an optical path in the vicinity of the pupil split prism 14. As mentioned above, this embodiment includes both the pupil split prism 14 and variable diaphragm 45; that is, both a function of splitting an entrance pupil that is to be implemented in a pupil split means and a function of varying the interval between centers of gravity. Mirrors 15 and 16 are installed to reflect beams deriving from light split by the pupil split prism 14. Solid-state imaging devices 19 and 20 such as CCDs are arranged at positions, at which the image formation lens 43 forms images, behind the mirrors 15 and 16.

In the optical system for the stereoscopic endoscope, the relay lens array 32 is composed of afocal relay lenses each projecting output with the magnification unchanged. In FIG. 7, only two lens are shown as the relay lens array 32 for simplification. The pupil split prism 14 is arranged so that the apex thereof will lie at a position conjugate with an entrance pupil formed by the objective lens array 11 and relay lens array 32. The variable diaphragm 45, which varies the interval between centers of gravity in two images deriving from a split entrance pupil by changing the position of a passing beam to displace an entrance pupil or by changing the diameter of the entrance pupil that has not been split, is located in the vicinity of the pupil split prism 14.

The pupil split prism 14 may be located not only at the position conjugate with the entrance pupil formed by the objective lens array 11 and relay lens array 32 but also at the entrance pupil position; that is, a position at which the objective lens array 11 and relay lens array 32 forms an entrance pupil, or a position near the entrance pupil position. The image formation lens 43 may include a zoom lens array or the like. The variable diaphragm 45 may be located not only in the vicinity of the position conjugate with the entrance pupil formed by the objective lens array 11 and relay lens array 32 but also at the entrance pupil location of the objective lens array 11 or the entrance pupil location of the relay lens array 32.

Figure 8A:
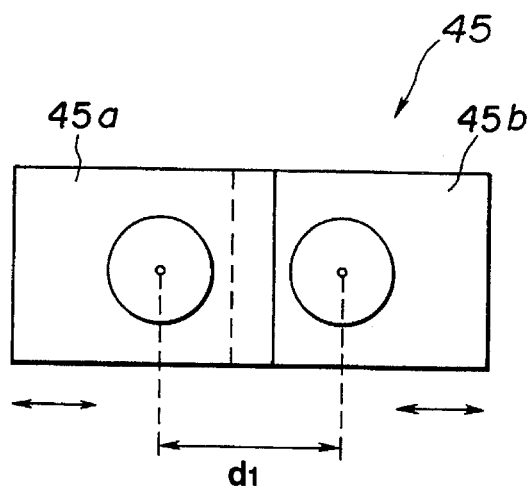
FIGS. 8(a) and 8(b) are an explanatory diagrams showing the first example of a structure of a variable diaphragm.
Figure 8B:
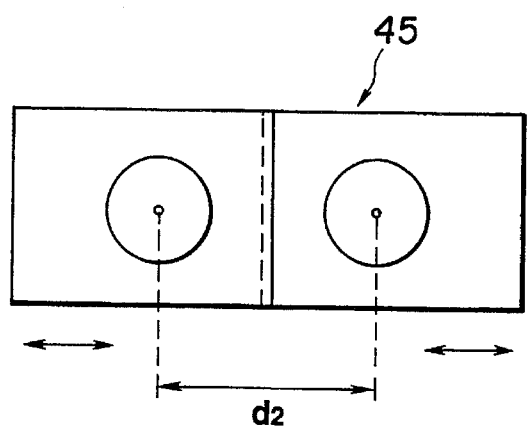

FIGS. 8(a) and 8(b) show the first example of a structure of the variable diaphragm 45. A diaphragm 45 of the first example is composed of two aperture plates 45a and 45b each having a circular aperture. Both or either of the aperture plates 47a and 47b is displaced in a direction perpendicular to the optical axis, thus changing the space between the apertures.

Figure 9A:
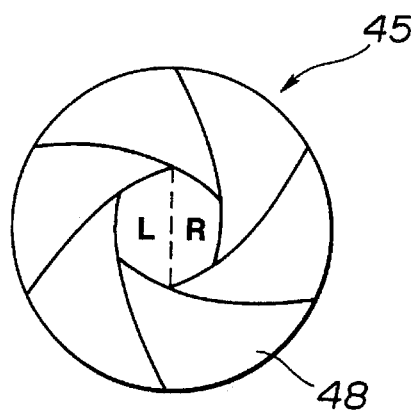
FIGS. 9(a) and 9(b) are an explanatory diagrams showing the second example of a structure of a variable diaphragm.
Figure 9B:
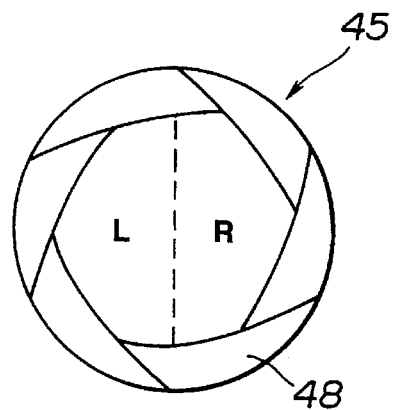

FIGS. 9(a) and 9(b) show the second example of the variable diaphragm 45. A diaphragm 45 of the second example has a plurality (six in this example) of aperture blades 48. The aperture blades 48 are displaced to vary the interval between centers of gravity in halves of a split entrance pupil.

The interval of centers of gravity in right and left halves of a split entrance pupil will be discussed below. When the pupil split prism 14 is used to halve an entrance pupil and provide right and left images having a parallax between them, If the entrance pupil is shaped like a circle, the interval between centers of gravity is defined as an intervals between the center of gravity in one of semicircular halves of the split circular pupil and the one of the other semicircular half. Repeatedly, the interval between centers of gravity is defined as an interval between centers of gravity in respective halves of a split entrance pupil.

One of factors determining three-dimensionality permitted by a stereoscopic endoscope is an angle of convergence formed by right and left optical systems. When the angle of convergence is large, three-dimensionality improves. When the angle of convergence is small, three-dimensionality deteriorates. When it comes to a pupil split optical system in which an image formed by one objective lens array is split into halves, it is appropriate that a ray passing through the center of gravity in each of the halves of a split entrance pupil is thought as an equivalent or the optical axis for determining the angle of convergence (internal angle formed by right and left optical systems). In this case, the length joining the centers of gravity in the halves of the entrance pupil is regarded as a space between the optical axes of the right and left optical systems. This means that three-dimensionality varies depending on the interval between centers of gravity in halves of a split entrance pupil.

The principle of this embodiment is that the aperture of the variable diaphragm 45 should vary so that the interval between centers of gravity will change according to the distance to a subject but three-dimensionality will remain constant irrelevant of the distance to a subject. Specifically, the aperture of the variable diaphragm 45 is varied in such a manner that when a subject lies at a near point, the interval between centers of gravity will diminish, and that when a subject lies at a far point, the interval between centers of gravity will increase.

To materialize the above principle, the diaphragm 47 of the first example shown in FIGS. 8(a), 8(b) or the diaphragm 48 of the second example shown in FIGS. 9(a), 9(b) is employed.

In the first example, either or both of the two aperture plates 45a and 45b are displaced in a direction perpendicular to the optical axis. The space between apertures therefore varies to change the positions of right and left entrance pupils. Accordingly, the interval between centers of gravity in the entrance pupils changes. For example, when an object at a near point is to be observed, as shown in FIG. 8a, the interval between centers of gravity in entrance pupils is narrowed to be $d_1$. When an object at a far point is to be observed, as shown in FIG. 8b, the interval between centers of gravity is widened to be $d_2$. When an object at a far point is to be observed after an object at a near point is, the interval between centers of gravity is widened from $d_1$ to $d_2$.

In the second example, a plurality of aperture blades 48 are displaced to vary the diameter of an aperture. The aperture opening is shaped substantially like a circle. An entrance pupil is always split right and left in the center thereof. The interval between centers of gravity in halves of a split entrance pupil varies with the change in the diameter of the aperture. For example, when an object at a near point is to be observed, as shown in FIG. 9a, the diameter of the aperture is shrunken to narrow the interval between centers of gravity in halves of a split entrance pupil. When an object at a far point is to be observed, as shown in FIG. 9b, the diameter of the aperture is expanded to widen the interval between centers of gravity in halves of a split entrance pupil. When an object at a far point is to be observed after an object at a near point is, the aperture is expanded from the state in FIG. 9a to the state in FIG. 9b. The interval between centers of gravity in halves of a split entrance pupil is thus increased.

Using the variable diaphragm 45, the interval between centers of gravity in right and left halves of a split entrance pupil can be varied. The angle of convergence is thus varied to control three-dimensionality. When an object at a far point is to be observed, the angle of convergence is increased to improve three-dimensionality. When an object at a near point is to be observed, the angle of convergence is reduced to deteriorate three-dimensionality. This realizes three-dimensional visualization with constant three-dimensionality regardless of the distance to a subject. Moreover, the interval between centers of gravity in right and left halves of a split entrance pupil can, if necessary, be changed to control three-dimensionality. Consequently, a desired sense of three-dimensionality can be provided for a certain distance of observation.

In other words, the three-dimensionality of a produced image can be controlled if necessary. Thus, three-dimensional visualization can be performed with desired three-dimensionality irrelevant of a distance to a subject.

The pupil split prism in the previous embodiments may be replaced with a means for splitting an entrance pupil using a porous plate. This kind of porous-plate type pupil split means can not only split an entrance pupil but also vary the interval between centers of gravity in halves of a split entrance pupil by displacing the holes. Thus, both the function of splitting an entrance pupil and a function of varying the interval between centers of gravity in halves of a split entrance pupil are realized with one united member. When a member for splitting an entrance pupil (pupil split prism) and a member for varying the interval between centers of gravity (variable diaphragm) are provided as independent members as mentioned in the previous embodiment, the plurality of members are made into a pupil split means to realize the function of splitting an entrance pupil and the function of varying the interval between centers of gravity.

Figure 10:
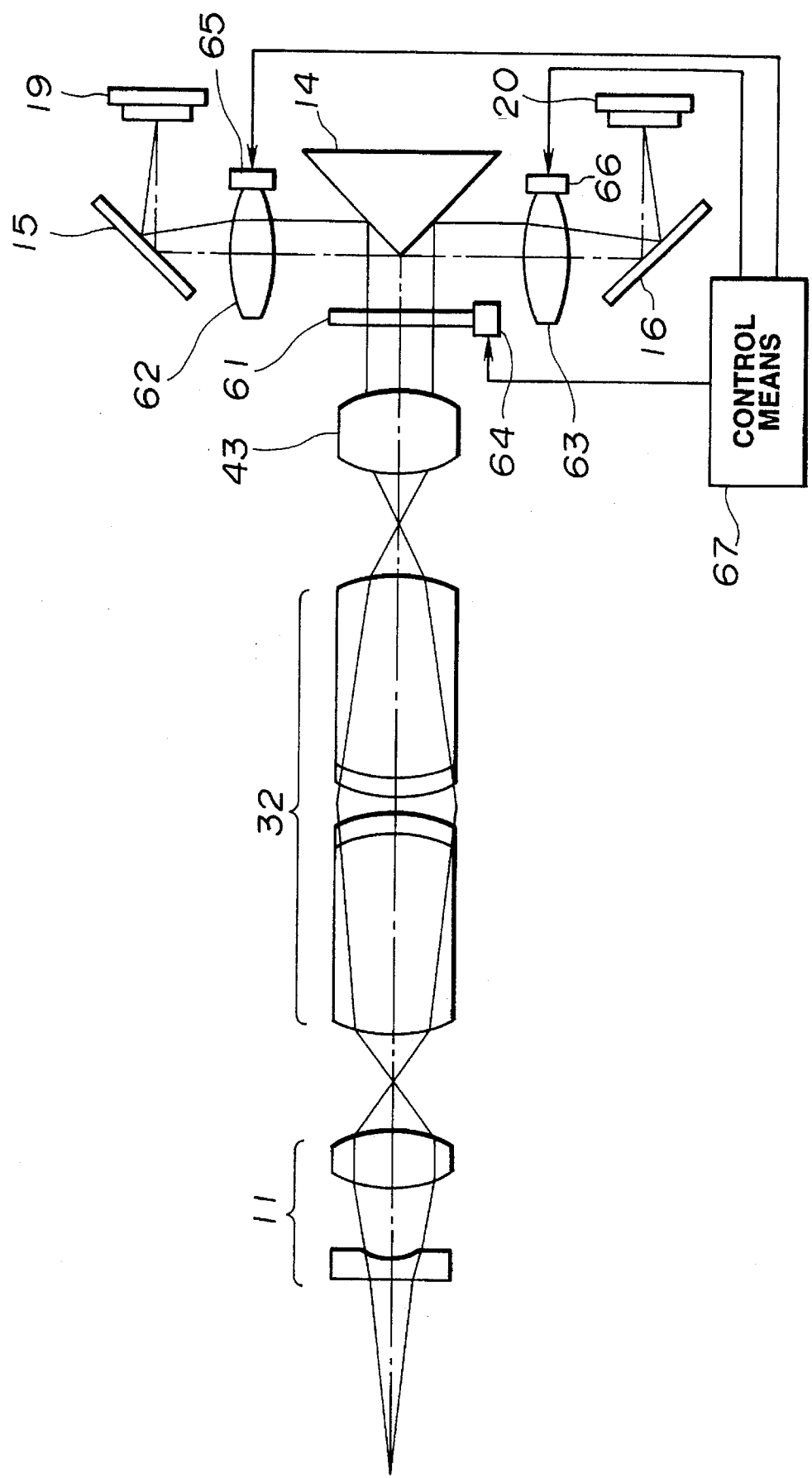
FIG. 10 is an explanatory diagram showing a configuration of a major portion of a stereoscopic endoscope relating to the fourth embodiment of the present invention.

FIG. 10 is an explanatory diagram showing a configuration of a major portion of a stereoscopic endoscope relating to the fourth embodiment of the present invention.

In the fourth embodiment, three-dimensionality control and focusing control, which have been implemented in the third embodiment, are interlocked with each other.

In a stereoscopic endoscope of the fourth embodiment, a variable diaphragm 61 similar to the variable diaphragm 45 in the third embodiment is installed in the vicinity of a pupil split prism 14 behind an image formation lens 43 in an optical system. Focusing lenses 62 and 63 for use in focusing are located in optical paths for beams deriving from an entrance pupil split by the pupil split prism 14. The other components in the optical system are identical to those in the third embodiment, of which description will be omitted.

Drives 64, 65, and 66 are coupled with the variable diaphragm 61, and the focusing lenses 62 and 63. The drives 64, 65, and 66 operate in response to instructions, which instruct a magnitude of varying a focus or a magnitude of varying an aperture, sent from a control means 67.

The control means 67 outputs a lens driving signal that specifies a magnitude of varying a focus according to a location of a subject and thus instructs the focusing lenses 62 and 63 to move until an in-focus state is attained. During the focusing control, a diaphragm driving signal for driving the variable diaphragm 61 by a specified magnitude is output to vary the interval between centers of gravity in right and left halves of a split entrance pupil. Thus, interlocked with focusing control, the variable diaphragm 61 is driven according to a distance to a subject that should be brought into focus. Consequently, the interval between centers of gravity in right and left entrance pupils is varied to stabilize the angle of convergence.

For example, when right and left images deriving from an entrance pupil are focused on a point at a given distance, if straight lines passing through the centers of gravity in the right and left images are regarded as optical axes, the optical axes are intersecting at the given point. Since the right and left optical axes create an angle of convergence and have a parallax between them, the right and left images are observed three-dimensionally. The focusing lenses 62 and 63 are then moved to change the focal lengths of the focusing lenses 62 and 63 from the above state to a state in which an object at a point, which is nearer than the given point, will be visualized three-dimensionally. Thus, the object at the near point can be brought into focus.

At this time, if the the interval between the centers of gravity in the right and left entrance pupils remains constant, since the angle of convergence varies, three-dimensionality changes. In the above case, since the subject has moved to the near point, three-dimensionality improves. In this embodiment, the variable diaphragm 61 for varying the interval between centers of gravity in right and left entrance pupils, and the focusing lenses 62 and 63 for achieving focusing are interlocked mutually. The angle of convergence can therefore be held constant irrelevant of the distance to a subject. Eventually, substantially the same three-dimensionality can be provided for visualization of all point from a far point to a near point.

As mentioned above, according to the present embodiment, three-dimensional visualization can be achieved with a desired distance brought into focus without varying the three-dimensionality of a produced image. Furthermore, an angle of convergence can be adjusted so as to provide desired three-dimensionality for a desired distance that is brought into focus.

Figure 11:
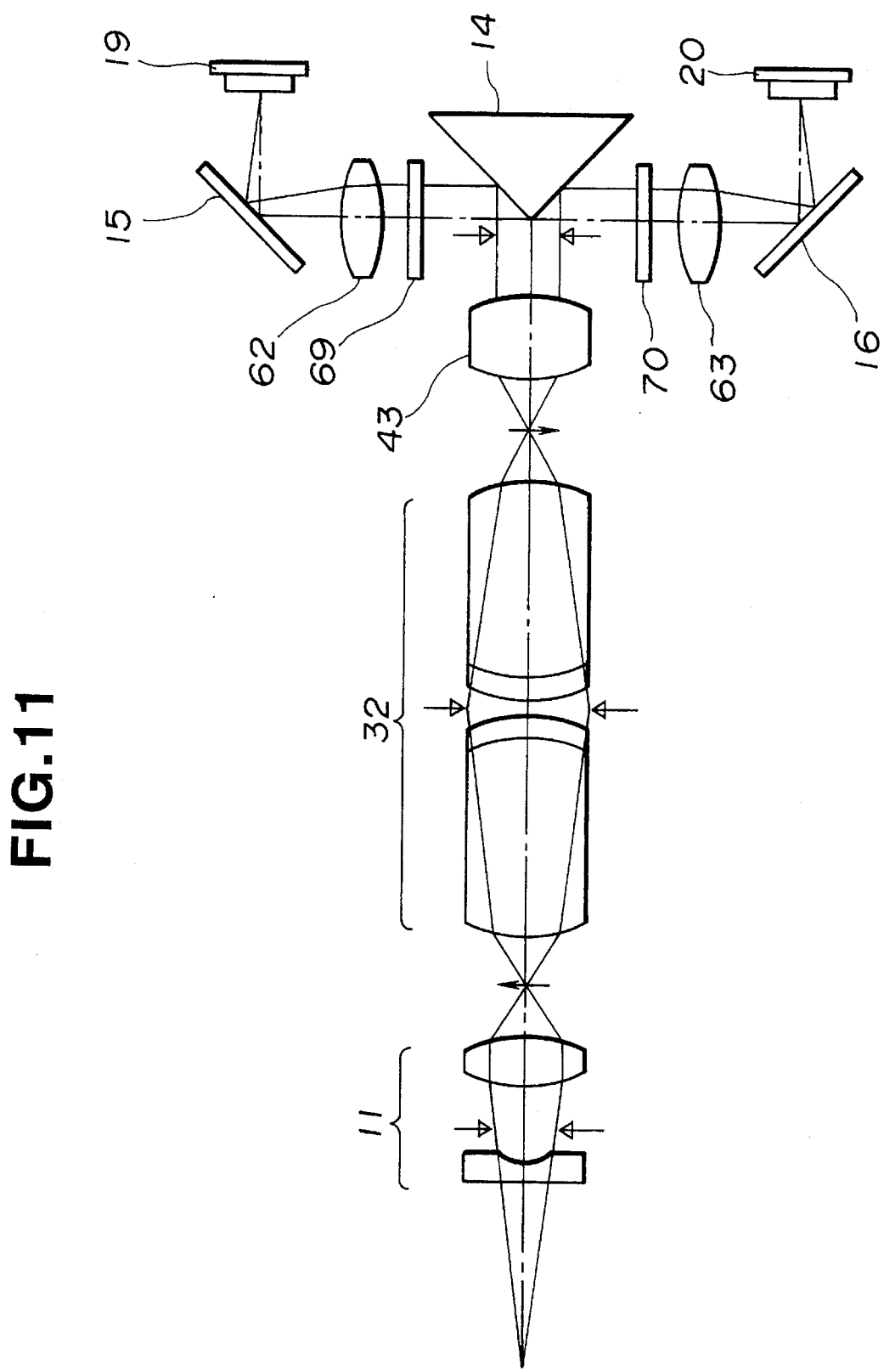
FIGS. 11 to 13 relate to the fifth embodiment of the present invention.
Figure 12:
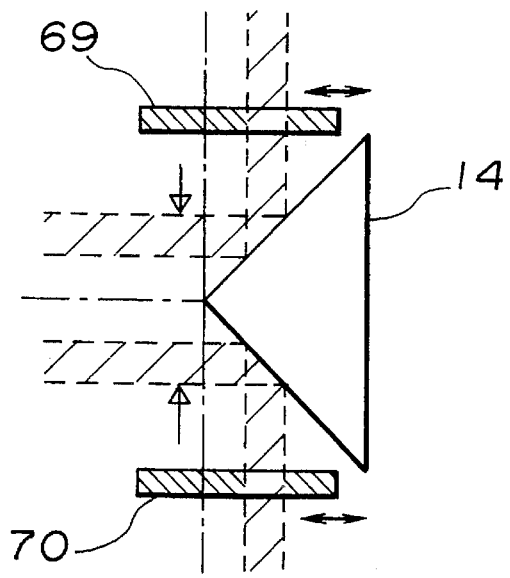
Figure 13:
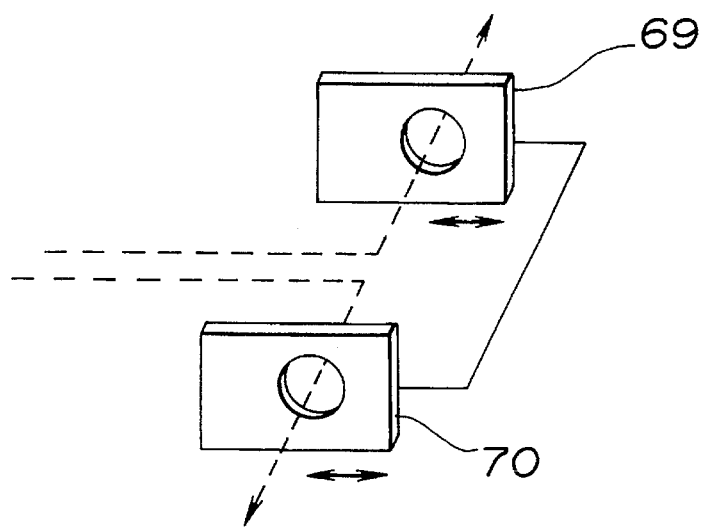

FIGS. 11 to 13 show the fifth embodiment of the present invention.

In the fifth embodiment, variable diaphragms are installed in optical paths for beams deriving from an entrance pupil split by a pupil split prism.

In a stereoscopic endoscope of the fifth embodiment, variable diaphragms 69 and 70 are installed in the right and left optical paths for beams deriving from an entrance pupil split by a pupil split prism 14 in an optical system. The other components are identical to those in the fourth embodiment, of which description will be omitted.

The variable diaphragms 69 and 70 are, as shown in FIGS. 12 and 13, formed with aperture plates each having an aperture. When the variable diaphragms 69 and 70 are displaced, the apertures move to change the entrance pupil positions or positions at which entrance pupils are formed. The variable diaphragms 69 and 70 transmit beams indicated with hatched areas in FIG. 12. When the variable diaphragms 60 and 70 move, the entrance pupil positions are displaced and the interval between the centers of gravity in the right and left entrance pupils varies. At this time, as shown in FIG. 13, since the variable diaphragms 69 and 70 are mutually coupled or the drives thereof are mutually interlocked, the two aperture plates are interlocked to move.

When the variable diaphragms 69 and 70 are moved forward along the optical axis of the portion of the optical system preceding the step of splitting an entrance pupil, the space between right and left entrance pupils; that is, the interval between the centers of gravity in the entrance pupils becomes narrower. The three-dimensionality of a produced image therefore deteriorates. On the other hand, when the variable diaphragms 69 and 70 are moved backward along the optical axis of the portion of the optical system preceding the step of splitting an entrance pupil, the space between the right and left entrance pupils is widened. The three-dimensionality of a produced image therefore improves. At this time, similarly to those in the fourth embodiment, the variable diaphragms 69 and 70, and the focusing lenses 62 and 63 are interlocked mutually.

As mentioned above, even when variable diaphragms are installed in optical paths for beams deriving from a split entrance pupil, the interval between centers of gravity in right and left entrance pupils can be adjusted in a similar manner as that in the third or fourth embodiment. Three-dimensional visualization can be achieved with constant three-dimensionality irrelevant of a distance to a subject.

Figure 14:
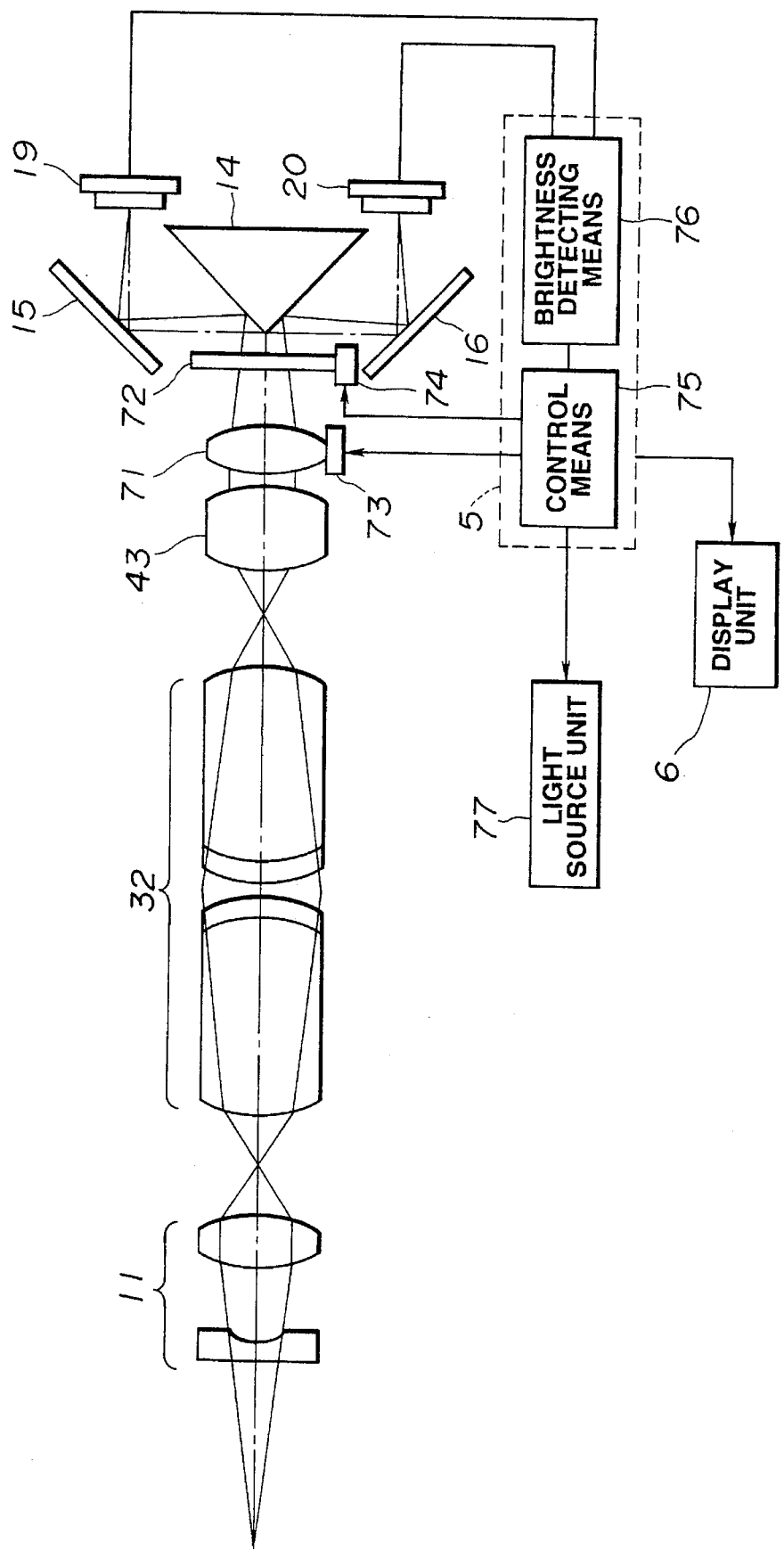
FIG. 14 is an explanatory diagram showing a configuration of a major portion of a stereoscopic endoscope relating to the sixth embodiment of the present invention.

FIG. 14 is an explanatory diagram showing a configuration of a major portion of a stereoscopic endoscope relating to the sixth embodiment of the present invention.

In the sixth embodiment, a distance detecting means for detecting a distance to a subject is included so that a variable diaphragm and a focusing lens can be controlled according to the detected distance.

In a stereoscopic endoscope of the sixth embodiment, a focusing lens 71 is installed behind an image formation lens 43 in an optical system. A variable diaphragm 72 is located in the vicinity of a pupil split prism 14. The other components of the optical system are identical to those in the third embodiment, of which description will be omitted. The variable diaphragm 72 is formed with, for example, the diaphragm 48 of the second example in the third embodiment which is designed to vary the diameter of the aperture thereof.

Drives 73 and 74 are coupled with the focusing lens 71 and variable diaphragm 72. The drives 73 and 74 operate in response to instructions, which are sent from a control means 75 incorporated in a signal processing unit 5, for specifying a magnitude of varying a focus and a magnitude of varying an aperture. The signal processing unit 5 further includes a brightness detecting means 76. The brightness detecting means 76 detects the brightness of an image in the output of solid-state imaging devices 19 and 20. The control means 75 and brightness detecting means 76 constitute an automatic light adjustment means for adjusting a quantity of light generated by a light source unit.

During observation under endoscopic guidance, illumination light is irradiated to a region to be observed. Due to this illumination method, the brightness of an image varies depending on a distance to a subject. The automatic light adjustment means is therefore used to detect the brightness of an image and control the quantity of light generated by the light source unit so that a certain level of brightness can be ensured. This means that a distance to a subject can be calculated using the detected brightness of an image. Specifically, when a subject lies at a near distance, the image is bright. When a subject lies at a far distance, the image is dark. A distance to a subject can therefore be calculated by detecting the brightness of the image thereof.

In this embodiment, the brightness detecting means 76 is used to detect the brightness of an image, and the control means 75 calculates a distance to a subject. Reflectances of objects, brightness levels of an image associated with quantities of illumination light generated by the light source unit 77, and distances to subjects associated with the brightness levels are pre-set and stored in a memory.

The brightness detecting means 76 uses an integrating means for integrating the output image signals of the solid-state imaging devices 19 and 20 to detect the brightness of an image, and outputs a brightness detected signal to the control means 75. The control means 75 calculates a distance to a subject using the brightness detected signal, determines a magnitude of moving the focusing lens 71 and a magnitude of varying the aperture of the variable diaphragm 72, which is interlocked with the focusing lens 71, according to the calculated distance, and then outputs a driving signal to each of the drives 73 and 74. Thus, in this embodiment, similarly to the fourth embodiment, focusing control is performed according to a distance to a subject. Interlocked with the focusing control, adjustment of the interval between centers of gravity in right and left entrance pupils is carried out. Three-dimensionality is thus controlled.

The relationship between a distance to a subject and an angle of convergence is predetermined depending on an optical system. Once magnitudes of moving the focusing lens 71 and magnitudes of varying the variable diaphragm 72, which is supposed to be interlocked with the focusing lens 71, are stored in a memory, the focusing lens 71 and variable diaphragm 72 are controlled to be interlocked with each other.

When a near point is to be observed, if the variable diaphragm 72, which can vary the diameter of the aperture thereof, is closed to narrow the interval between centers of gravity in right and left entrance pupils, the diameter of the aperture decreases to suppress the brightness of an image. That is to say, three-dimensionality control and image brightness control can be interlocked with each other. When the variable diaphragm 72 is displaced, the control means 75 outputs a light value adjustment signal to the light source unit 77 and thus executes light value adjustment for the light source.

As mentioned above, according to the present embodiment, automatic light adjustment control, focusing control, and three-dimensionality control can be interlocked with one another. When a near point is observed, the image used to exhibit a small depth of field. However, when the variable diaphragm 72 is employed, since the diameter of the aperture thereof can be shrunken, a near point is visualized with a large depth of field.

A relay optical system in any of the third to sixth embodiments has one optical axis. Alternatively, the relay optical system may be designed so that a transmitted image is split in the middle of the system and then transmitted farther. The optical system may include an image formation lens, a zoom lens, and so on.

In the present invention, it will be apparent that a wide range of different working modes can be formed on the basis of the invention without departing from the spirit and scope of the invention. This invention is limited to the appended claims but not restricted to any specific working modes.

What is claimed is:

1. A stereoscopic endoscope, comprising:

an objective lens array having one optical axis;

a relay lens array for transmitting an object image produced by said objective lens array, said relay lens array including an afocal system;

a pupil split means that is located at or near a position of a pupil of said relay lens array or a position conjugate to said position, wherein said pupil split means splits said pupil into a plurality of portions;

an image formation optical system that receives a beam emanating from said relay lens array and forms a plurality of object images in cooperation with said pupil split means; and imaging means for receiving said object images.

2. A stereoscopic endoscope comprising:

an objective lens array having one optical axis;

a relay lens array that is located coaxially with said objective lens array and that transmits an object image produced by said objective lens array;

a pupil split means that splits a pupil of said relay lens array according to a difference area ratio depending on whether light originates from the center of a field of view or the perimeter of a field of view, wherein said pupil split means halves a pupil of said relay lens array, and the ratio of the quantities of light in the halves of the split entrance pupil is 1 to 1 for light originating from the center of a field of view, but it is larger than 1 to 0.3 for light originating from the perimeter of a field of view;

an image formation optical system that receives a beam emanating from said relay lens array and forms a plurality of object images in cooperation with said pupil split means; and imaging means for receiving said object images.

3. A stereoscopic endoscope comprising:

an objective lens array having one optical axis;

a relay lens array that is located coaxially with said objective lens array and that transmits an object image produced by said objective lens array;

a pupil split means that splits a pupil of said relay lens array into a plurality of portions and varies the interval between centers of gravity in said plurality of pupils, wherein a focusing lens is installed in the incident side of said pupil split means;

an image formation optical system that receives a beam emanating from said relay lens array and forms a plurality of object images in cooperation with said pupil split means; and imaging means for receiving said object images.

4. A stereoscopic endoscope comprising:

an objective lens array having one optical axis;

a relay lens array that is located coaxially with said objective lens array and that transmits an object image produced by said objective lens array;

a pupil split means that splits a pupil of said relay lens array into a plurality of portions and varies the interval between centers of gravity in said plurality of pupils;

an image formation optical system that receives a beam emanating from said relay lens array and forms a plurality of object images in cooperation with said pupil split means, wherein said image formation optical system includes a focusing lens that is movable along the optical axis, and the movement of the focusing lens is interlocked with the variation of the interval between centers of gravity in said plurality of pupils that is performed by said pupil split means; and imaging means for receiving said object images.

5. A stereoscopic endoscope comprising:

an objective lens array having one optical axis;

a relay lens array that is located coaxially with said objective lens array and that transmits an object image produced by said objective lens array;

a pupil split means that splits a pupil of said relay lens array into a plurality of portions and varies the interval between centers of gravity in said plurality of pupils;

an image formation optical system that receives a beam emanating from said relay lens array and forms a plurality of object images in cooperation with said pupil split means, wherein said image formation optical system includes a focusing lens that is movable along the optical axis and wherein said image formation optical system further includes a focusing and pupil interval control means by which focusing control for controlling drive of said focusing lens is interlocked with control of variation of the interval between centers of gravity in said plurality of pupils that is performed by said pupil split means; and imaging means for receiving said object images.

6. A stereoscopic endoscope according to claim 5, further including a distance detecting means for detecting a distance to an object, wherein:

said focusing and pupil interval control means performs focusing control and control of variation of the interval between centers of gravity in pupils according to the distance to an object detected by said distance detecting means.

7. A stereoscopic endoscope according to claim 6, wherein said distance detecting means includes a brightness detecting means for detecting the brightness of an object image in the output of said imaging means.

8. A stereoscopic endoscope comprising:

an objective lens array having one optical axis;

a relay lens array that is located coaxially with said objective lens array and that transmits an object image produced by said objective lens array;

a pupil split means that splits a pupil of said relay lens array into a plurality of portions and varies the interval between centers of gravity in said plurality of pupils, wherein said pupil split means includes a diaphragm member having a plurality of apertures, and said plurality of apertures are displaced in directions perpendicular to the optical axis in order to vary the interval between centers of gravity in said pupils;

an image formation optical system that receives a beam emanating from said relay lens array and forms a plurality of object images in cooperation with said pupil split means; and imaging means for receiving said object images.

9. A stereoscopic endoscope comprising:

an objective lens array having one optical axis;

a relay lens array that is located coaxially with said objective lens array and that transmits an object image produced by said objective lens array;

a pupil split means that splits a pupil of said relay lens array into a plurality of portions and varies the interval between centers of gravity in said plurality of pupils, wherein said pupil split means includes a diaphragm member having an aperture whose size is variable with the optical axis of said relay lens array as a center, and the size of said aperture is changed to vary the interval between centers of gravity in said plurality of pupils;

an image formation optical system that receives a beam emanating from said relay lens array and forms a plurality of object images in cooperation with said pupil split means; and imaging means for receiving said object images.

10. A stereoscopic endoscope comprising:

an objective lens array having one optical axis;

a relay lens array that is located coaxially with said objective lens array and that transmits an object image produced by said objective lens array;

a pupil split means that splits a pupil of said relay lens array into a plurality of portions and varies the interval between centers of gravity in said plurality of pupils, wherein said pupil split means includes an optical element for branching a beam emanating from said relay lens array, and diaphragm members that are arranged in optical paths for branching beams, and wherein the apertures of the respective diaphragm members are displaced in directions perpendicular to the optical axis in order to change the positions of said pupils;

an image formation optical system that receives a beam emanating from said relay lens array and forms a plurality of object images in cooperation with said pupil split means; and imaging means for receiving said object images.

11. A stereoscopic endoscope, comprising:

an objective lens array having one optical axis;

a relay lens array that is located coaxially with said objective lens array, and that relays an image produced by said objective lens array and re-forms an object image at a specified position;

an aperture stop means having a plurality of apertures for forming pupils at positions off the optical axis of said relay lens array; and imaging means for receiving images produced with beams passing through said apertures for forming pupils in said aperture stop means.

12. A stereoscopic endoscope according to claim 11, wherein said image formation optical system has a zoom function.

13. A stereoscopic endoscope according to claim 11, wherein said apertures for forming pupils are shaped like approximate circles.

14. A stereoscopic endoscope according to claim 11, wherein sizes of said plurality of apertures for forming pupils are approximately equal.

15. A stereoscopic endoscope, comprising:
   an objective optical system for producing an object image;
   a relay optical system for relaying an image produced by said objective optical system;
   an image formation lens system that is located behind the image relayed by said relay optical system and that converges light emanating from said relay optical system;
   a pupil split means that is located behind said image formation lens system and that splits a beam emanating from said relay optical system into a plurality of beams; and
   imaging means for receiving said splitting beams.

16. A stereoscopic endoscope according to claim 15, wherein said image formation optical system has a focus function.

17. A stereoscopic endoscope system comprising:
   an objective lens array having one optical axis;
   a relay lens array that is located coaxially with said objective lens array, which relays an image produced by said objective lens and re-forms an object image at a specified position;
   an aperture stop means having a plurality of apertures for forming pupils at positions off the optical axis of said relay lens array; and
   imaging means for receiving images produced with beams passing through said apertures for forming pupils in said aperture stop means;
   and wherein:
      an insertion part containing said objective lens array and relay lens array;
      a forceps part containing said imaging means and connected with said insertion part;
      a signal cable extended from said forceps parts;
      a signal processing part connected with said cable; and
      a display unit connected with said signal processing part.

18. A stereoscopic endoscope system according to claim 17, wherein said display unit includes a CRT and images of right and left are sequentially switched and displayed on the CRT, and said stereoscopic endoscope system further comprising glasses for stereoscopically observing right and left images displayed on said CRT.

* * * * *